(12) United States Patent
Roberts et al.

(10) Patent No.: US 12,083,382 B2
(45) Date of Patent: Sep. 10, 2024

(54) MIRROR THERAPY DEVICE

(71) Applicant: Institute of Technology Sligo, Ballinode (IE)

(72) Inventors: David Roberts, Sligo (IE); Kenneth Monaghan, Sligo (IE); Monika Ehrensberger, Tubbercurry (IE); Daniel Simpson, Carney (IE)

(73) Assignee: Atlantic Technological University, Sligo (IE)

( * ) Notice: Subject to any disclaimer, the term of this patent is extended or adjusted under 35 U.S.C. 154(b) by 127 days.

(21) Appl. No.: 17/632,355

(22) PCT Filed: Jul. 31, 2020

(86) PCT No.: PCT/EP2020/071737
§ 371 (c)(1),
(2) Date: Feb. 2, 2022

(87) PCT Pub. No.: WO2021/023677
PCT Pub. Date: Feb. 11, 2021

(65) Prior Publication Data
US 2022/0288449 A1    Sep. 15, 2022

(30) Foreign Application Priority Data

Aug. 2, 2019   (GB) ...................... 1911092

(51) Int. Cl.
*A63B 23/035*    (2006.01)
*A61F 2/50*      (2006.01)
(Continued)

(52) U.S. Cl.
CPC .................. *A63B 23/03508* (2013.01); *A63B 21/00058* (2013.01); *A63B 21/00178* (2013.01);
(Continued)

(58) Field of Classification Search
CPC ........ A63B 21/00058; A63B 21/00178; A63B 21/0058; A63B 21/02; A63B 21/04;
(Continued)

(56) References Cited

U.S. PATENT DOCUMENTS 4,863,163 A * 9/1989 Wehrell ................... A63B 5/16
482/129
2008/0306572 A1   12/2008 Osada et al.
(Continued)

FOREIGN PATENT DOCUMENTS

DE    102006013877    9/2007
EP       0344723      12/1989
(Continued)

OTHER PUBLICATIONS

Quick fix therapy mirror—therapy equipment from Smirthwaite, https://www.smirthwaite.co.uk/product/quick-fix-mirror/, printed on Jul. 20, 2020, 2 pages.
(Continued)

*Primary Examiner* — Zachary T Moore
(74) *Attorney, Agent, or Firm* — LaBatt, LLC (57) ABSTRACT

A portable mirror therapy device comprises a stiff divider panel attached to a base unit which supports the divider panel in an upright position to define two adjacent limb receiving spaces at opposite sides of the divider panel. A mirror is mounted on one face of the divider panel. A clamp mounted at a lower end of the divider panel cooperates with an underside of the base unit for securing the base unit on a support such as a table or worktop. An exercise apparatus is mounted on the device and includes a limb engaging member, which in this case comprises a handle at a mirror side of the divider panel. The exercise apparatus is a resistance load training system and comprises a load cord extending from the handle to an associated resistance element mounted
(Continued)

within a housing on an opposite side of the divider panel to the mirror.

19 Claims, 8 Drawing Sheets

(51) Int. Cl.
*A63B 21/00* (2006.01)
*A63B 21/005* (2006.01)
*A63B 21/04* (2006.01)
*A63B 21/16* (2006.01)

(52) U.S. Cl.
CPC ...... *A63B 21/0057* (2013.01); *A63B 21/0058* (2013.01); *A63B 21/0442* (2013.01); *A63B 21/16* (2013.01); *A63B 21/4035* (2015.10); *A61F 2002/5064* (2013.01); *A61H 2201/1635* (2013.01); *A63B 2220/16* (2013.01); *A63B 2220/833* (2013.01); *A63B 2225/09* (2013.01); *A63B 2225/12* (2013.01); *A63B 2225/50* (2013.01)

(58) Field of Classification Search
CPC ..... A63B 21/055; A63B 21/05; A63B 21/153; A63B 21/1618; A63B 21/1636; A63B 21/4019; A63B 21/4027; A63B 21/4035; A63B 23/03508
See application file for complete search history.

(56) References Cited

U.S. PATENT DOCUMENTS

| 2011/0300994 | A1 | 12/2011 | Verkaaik et al. |
| 2015/0313793 | A1 | 11/2015 | Lee et al. |
| 2016/0067548 | A1* | 3/2016 | Shiao ............... A63B 21/0058 482/5 |
| 2016/0121160 | A1 | 5/2016 | Hyslop et al. |
| 2017/0304137 | A1 | 10/2017 | Sugihara et al. |
| 2018/0221698 | A1* | 8/2018 | Heathfield ......... A63B 21/4047 |

FOREIGN PATENT DOCUMENTS

| JP | 2007105411 | 4/2007 |
| JP | 2016214343 | 12/2016 |
| WO | 2009125347 | 10/2009 |
| WO | 2010059066 | 5/2010 |

OTHER PUBLICATIONS

International Search Report and Written Opinion for International Application No. PCT/EP2020/071737, Dec. 22, 2020, 15 pages.
Search Report for UK Patent Application No. GB1911092.3, Jan. 20, 2020, 1 page.

* cited by examiner

MIRROR THERAPY DEVICE

INTRODUCTION

The present invention relates to a neural therapy device which incorporates the use of a mirror for rehabilitation of a human subject with a debilitated or absent limb and more specifically, limbs debilitated by reduced mobility, chronic neurologic pain, phantom pain or orthopaedic damage. These conditions can be a result of a stroke, limb amputation, partial paralysis or bone fractures.

BACKGROUND ART

The concept of mirror therapy was initially developed to treat amputees with phantom limb pain, but the therapy has found further use for multiple neurologic and mobility disorders of the limbs. A conventional mirror therapy device will typically be designed with a box, cloak or other means for hiding a subject's debilitated limb and a mirror. The mirror divides the subject's opposing limbs, with the mirrored surface facing the healthy limb. A therapy method usually involves the subject moving their healthy limb in front of the mirror to create a reflected image which the subject perceives to be their hidden, debilitated limb. This stimulates a motor neuron response from the brain to the debilitated limb muscles to replicate the movement seen in the mirror image, helping to rehabilitate the debilitated limb by strengthening the damaged neural pathways.

However, existing mirror therapy devices have limitations. Current designs are typically static devices limited to mirror therapy. Also, it is often very inconvenient for a person to travel to and from a clinic on a regular basis. Many patients will live a considerable distance from the clinic which creates a difficulty for regular attendance at the clinic. There is a cost associated with travel to and from the clinic. Also many patients cannot travel on their own and require the assistance of a carer. Factors such as limited clinician time, transport difficulties of debilitated subjects and infrequent therapy sessions all impact the efficacy of the therapy. Another limitation is the lack of traceable progress with current devices. Also current post stroke therapy support generally ceases within 12 months of hospital discharge and does not allow for a sustained therapy plan.

A mirror therapy device is disclosed in US 2018/0221698 A1 having an upstanding mirror mounted on a support stand which sits on a tabletop or on a floor in use. A user grips handles on opposite sides of the mirror to push and pull a wheel mounted within a housing on which the mirror is mounted. JP 2007105411 A discloses another mirror therapy device comprising a mirror upstanding on a base whit sits on a tabletop in use. Air filled resilient bags on opposite sides of the mirror are interconnected by a tube to allow air transfer between the bags. A user grips both bags and by squeezing and releasing the bag gripped by the healthy hand can open and close the injured hand on the other bag at an opposite side of the mirror to give a gripping tactile sensation to the injured hand for rehabilitation purposes.

The present invention is directed towards providing an improved mirror therapy device.

SUMMARY OF THE INVENTION

According to the invention there is provided a portable therapy device for use in limb rehabilitation of a subject, the device comprising a divider panel, a base unit to support the divider panel in an upright position to define two adjacent limb receiving spaces at opposite sides of the divider panel, a mirror on one face of the divider panel, and an attachment device for securing the base unit to a support.

In one embodiment of the invention the attachment device is demountably engagable with the support.

In another embodiment of the invention the mirror therapy device includes an exercise apparatus which includes a limb engaging member at a mirror side of the divider panel.

In another embodiment of the invention the exercise apparatus is a resistance load training system.

In another embodiment of the invention the resistance load training system comprises a load cord extending from the limb engaging member to a resistance element.

In another embodiment of the invention the load cord is articulated through an aperture in the divider panel, the resistance element being mounted on an opposite side of the divider panel to the mirror.

In another embodiment of the invention the load cord is movable between a retracted position and an extended position, the load cord being biased towards the retracted position, means being provided to control the rate at which the load cord returns from the extended position to the retracted position.

In another embodiment of the invention the resistance element has a motor, a gearbox and clutch arrangement to control the rate at which the load cord returns from the extended portion to the retracted position.

In another embodiment of the invention the attachment device is adjustable.

In another embodiment of the invention the attachment device is movable between an engaged position with the support and a release position.

In another embodiment of the invention the attachment device has an actuating switch to switch the attachment device between the engaged position and the release position.

In another embodiment of the invention the attachment device is a clamp.

In another embodiment of the invention the mirror therapy device includes one or more sensors associated with the exercise apparatus and/or the patient to sense selected operating parameters of the exercise apparatus and/or take selected physiological measurements of the patient, the sensors being connected to an associated controller.

In another embodiment of the invention the controller is operable to record data received from the sensors.

In another embodiment the physiological measurements include patient neural activity.

In another embodiment the sensor and controller are operable to record the distance travelled by the load cord.

In another embodiment the sensor and the controller are operable to record the position of the limb engaging member.

In another embodiment the sensor and the controller are operable to record the flexion angle of a wrist of a patient's hand holding the limb engaging member.

In another embodiment of the invention the controller is connected to a display screen on the divider panel to display sensed data to a patient using the mirror therapy device.

In another embodiment of the invention the controller is operable to transmit data collected to a remote location.

In another embodiment of the invention means is provided for remotely controlling the exercise apparatus.

In another embodiment of the invention the divider panel is adjustable on the base unit.

In another embodiment of the invention the divider panel is hingedly connected to the base unit for tilting the divider panel on the base unit.

In another embodiment of the invention the portable mirror therapy device comprises a motor linked to a gearbox and clutch contained in a housing mounted on the non-mirrored side of the divider panel, wherein the clutch is mechanically connected to a pulley guided load cord which passes through an aperture in the divider panel and mirror, a grip handle at a free end of the cord constructed from non-slip material, sensors which detect user limb data during exercise and transfer the data electronically to a processor of the controller contained in the housing which includes a transmitter and receiver to wirelessly send data to remote processors, a set of adjustable screw handle clamps attached to the base unit and divider panel, a recessed handle in the divider panel and a carry case for reception and transport of the mirror therapy device.

BRIEF DESCRIPTION OF THE DRAWINGS

The invention will be more clearly understood by the following description of some embodiments thereof, given by way of example only, with reference to the accompanying drawings, in which.

DETAILED DESCRIPTION OF THE PREFERRED EMBODIMENTS

Figure 1:
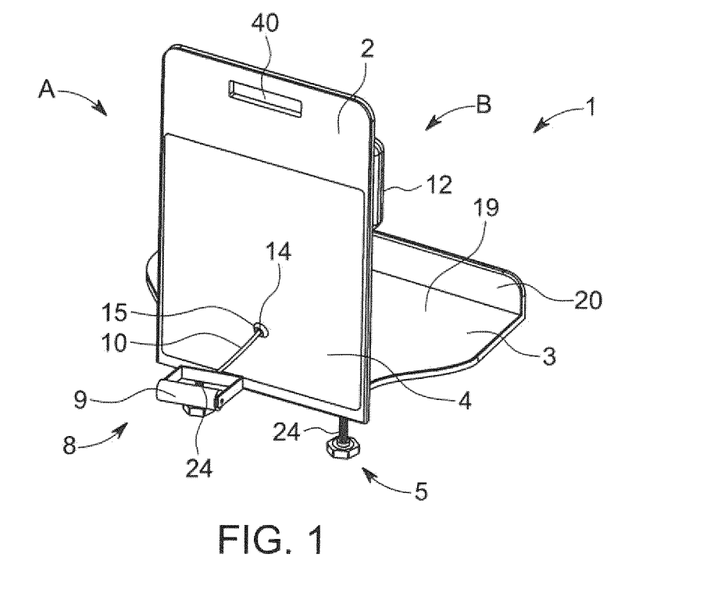
FIG. 1 is a perspective view of a mirror therapy device according to the invention.
Figure 2:
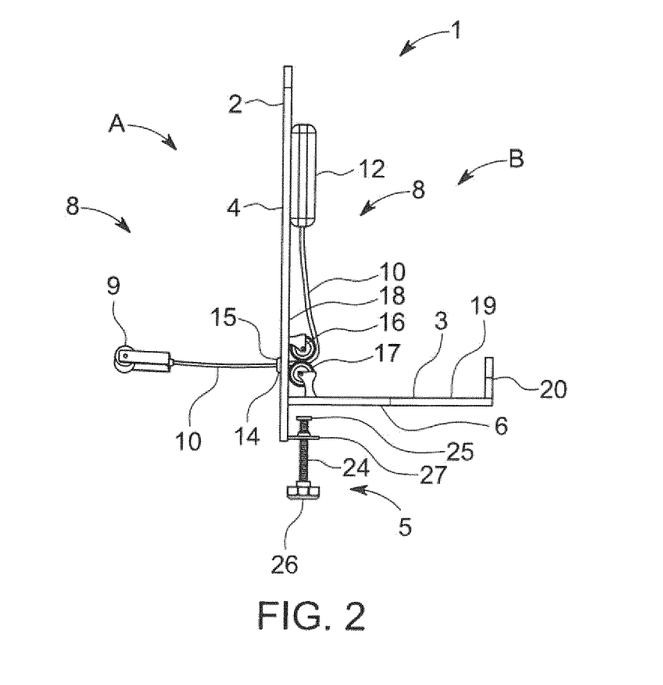
FIG. 2 is a side elevational view of the mirror therapy device.
Figure 3:
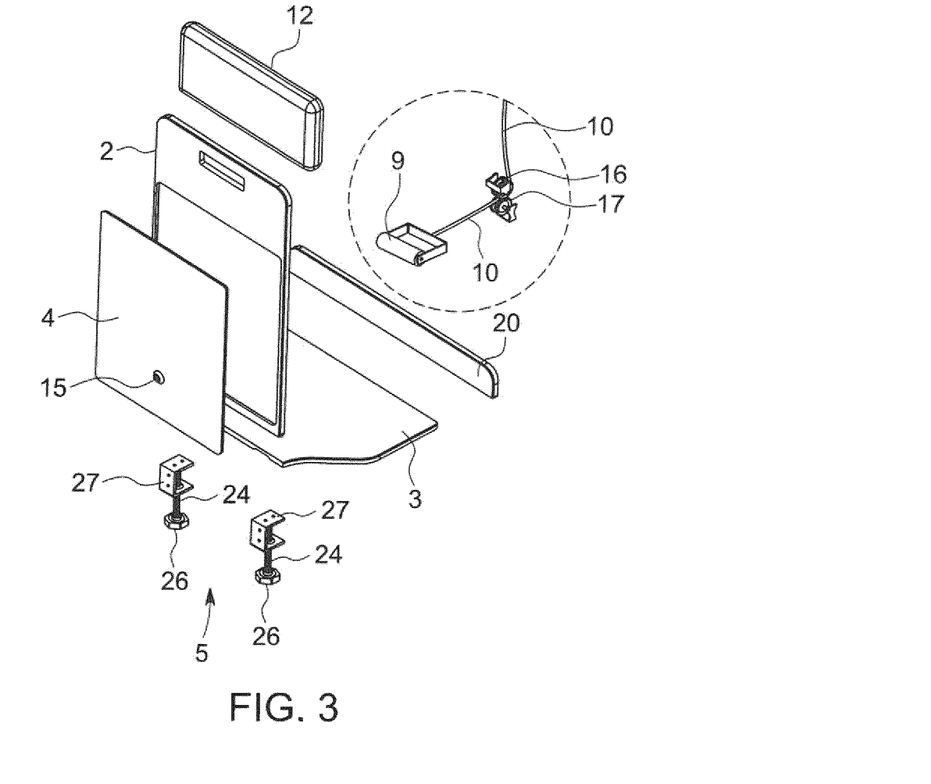
FIG. 3 is an exploded perspective view of the mirror therapy device.
Figure 4:
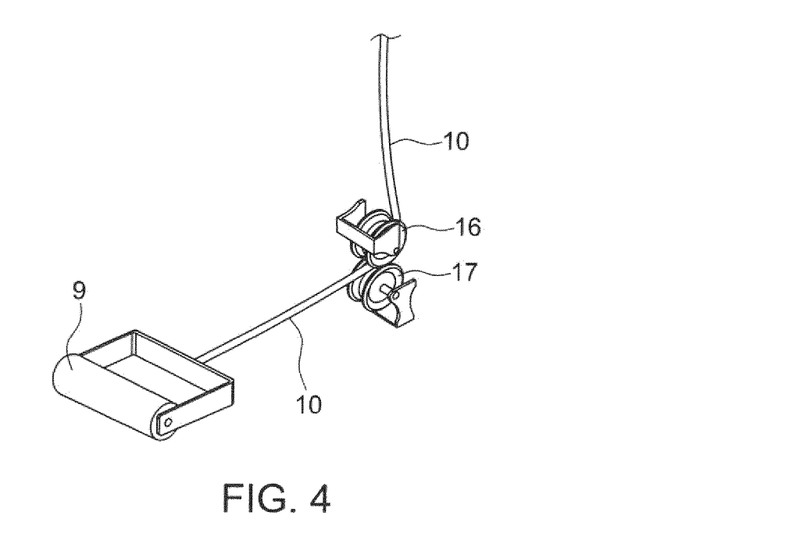
FIG. 4 is an enlarged detail view showing portion of the mirror therapy device.
Figure 5:
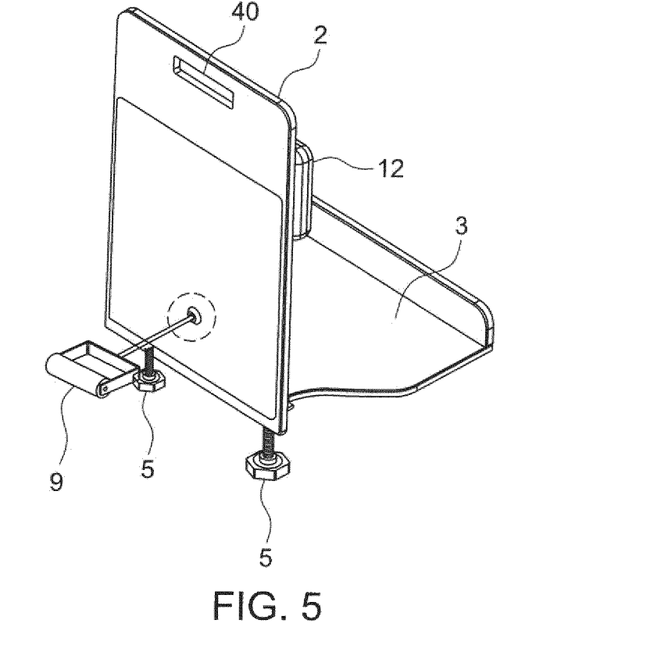
FIG. 5 is a perspective view of the mirror therapy device.
Figure 6:
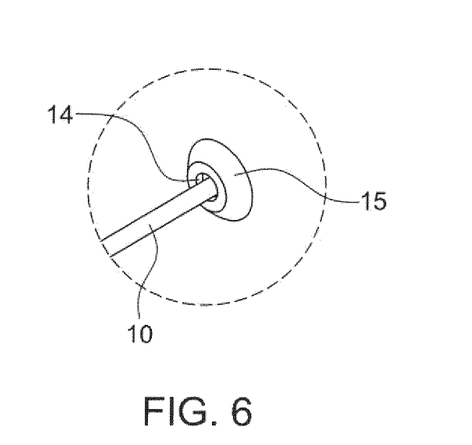
FIG. 6 is an enlarged detail view showing a portion of the mirror therapy device.
Figure 7:
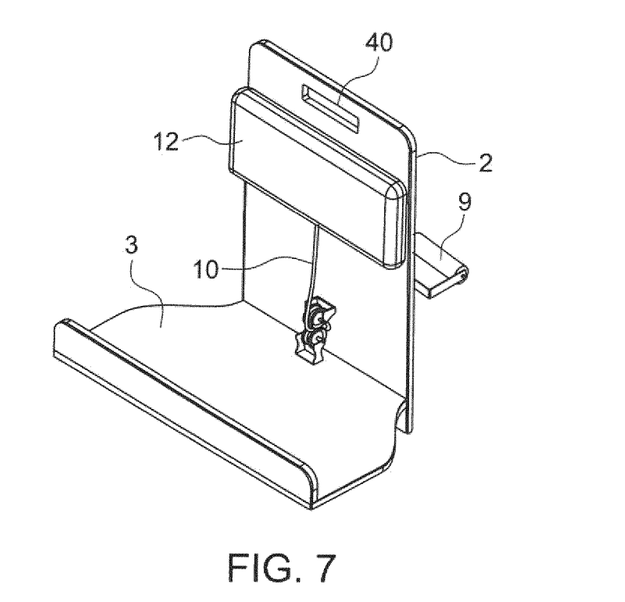
FIG. 7 is a perspective view of the mirror therapy device.
Figure 8:
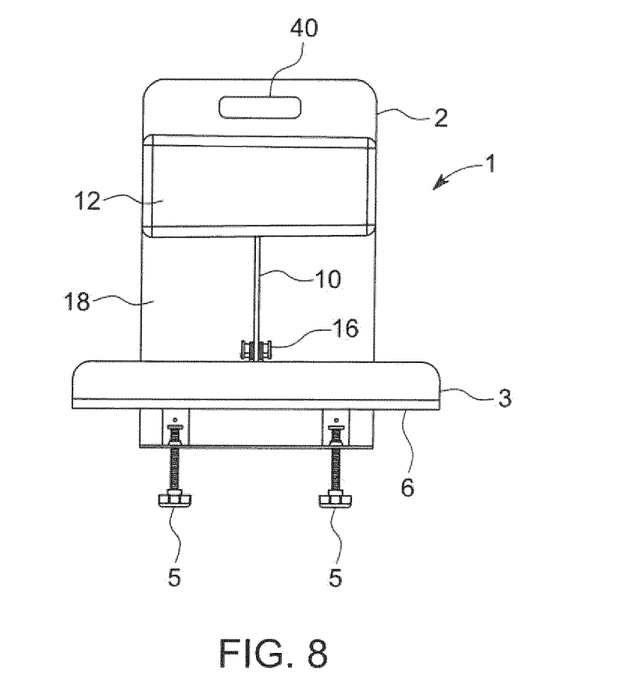
FIG. 8 is an elevational view of the mirror therapy device.
Figure 9:
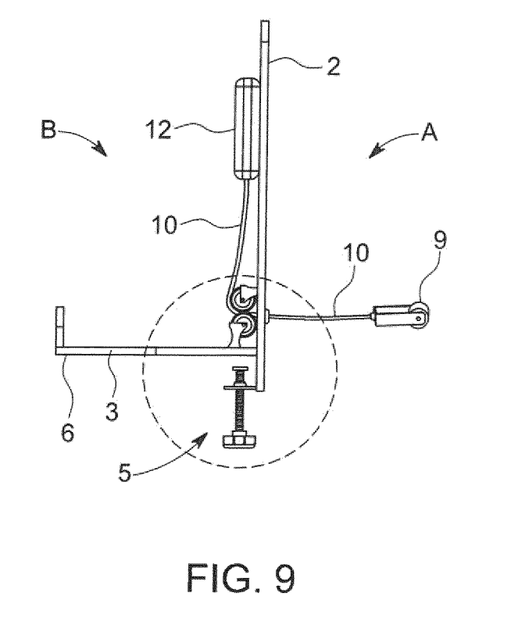
FIG. 9 is a side elevational view of the mirror therapy device.
Figure 10:
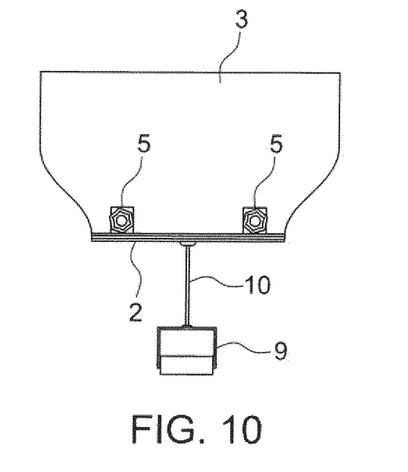
FIG. 10 is an underneath plan view of the mirror therapy device.
Figure 11:
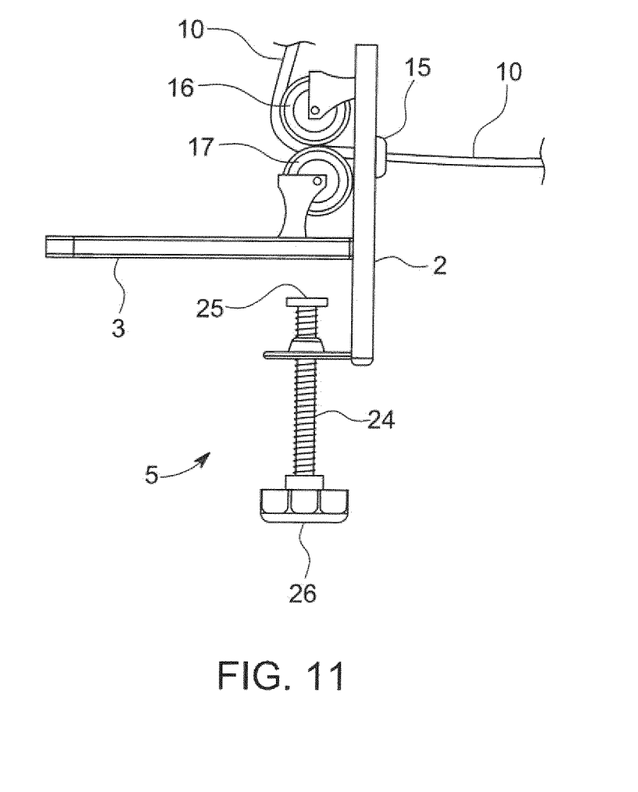
FIG. 11 is an enlarged detail side sectional elevational view showing portion of the device.

Referring to the drawings, there is illustrated a mirror therapy device according to the invention indicated generally by the reference numeral 1. The portable mirror therapy device 1 comprises a stiff divider panel 2 attached to a base unit 3 which supports the divider panel 2 in an upright position to define two adjacent limb receiving spaces A, B (FIG. 2) at opposite sides of the divider panel 2. A mirror 4 is mounted on one face of the divider panel 2. A clamp, indicated generally by the reference numeral 5, mounted at a lower end of the divider panel 2 cooperates with an underside 6 of the base unit 3 for rigidly securing the base unit 3 on a support such as a table or worktop. An exercise apparatus 8 is mounted on the device 1 and includes a limb engaging member, which in this case comprises a handle 9 at a mirror side of the divider panel 2.

The exercise apparatus 8 is a resistance load training system and comprises a load cord 10 extending from the handle 9 to an associated resistance element 11 (FIG. 12) mounted within a housing 12 on an opposite side of the divider panel 2 to the mirror 4, that is on a rear face 18 of the divider panel 2. The load cord 10 is articulated through an aperture 14 in the divider panel 2, passing through a rubber or plastics grommet 15 mounted in the aperture 14 to avoid chaffing of the cord 10. Guide pulleys 16, 17 mounted on the rear face 18 of the divider panel 2 and on an upper face 19 of the base unit 3 guide the load cord 10 through 90° with minimal friction for delivery up to the resistance element 11 in the housing 12 at a top of the rear face 18 of the divider panel 2.

In this case the base unit 3 is essentially a horizontal platform extending outwardly from a lower end of the rear face 18 of the divider panel 2, perpendicular to the divider panel 2.

The clamp 5 comprises two spaced-apart clamp bolts 24 each having a clamp disc 25 at an inner end and a handle 26 at the outer end. Each clamp bolt 24 screws through an associated mounting bracket 27 adjacent a bottom of the rear face 18 of the divider panel 2 below the base unit 3. Each clamp disc 25 cooperates with the underside 6 of the base unit 3 to clamp a table or worktop between the clamp 5 and the underside 6 of the base unit 3 which sits on top of the table.

Figure 12:
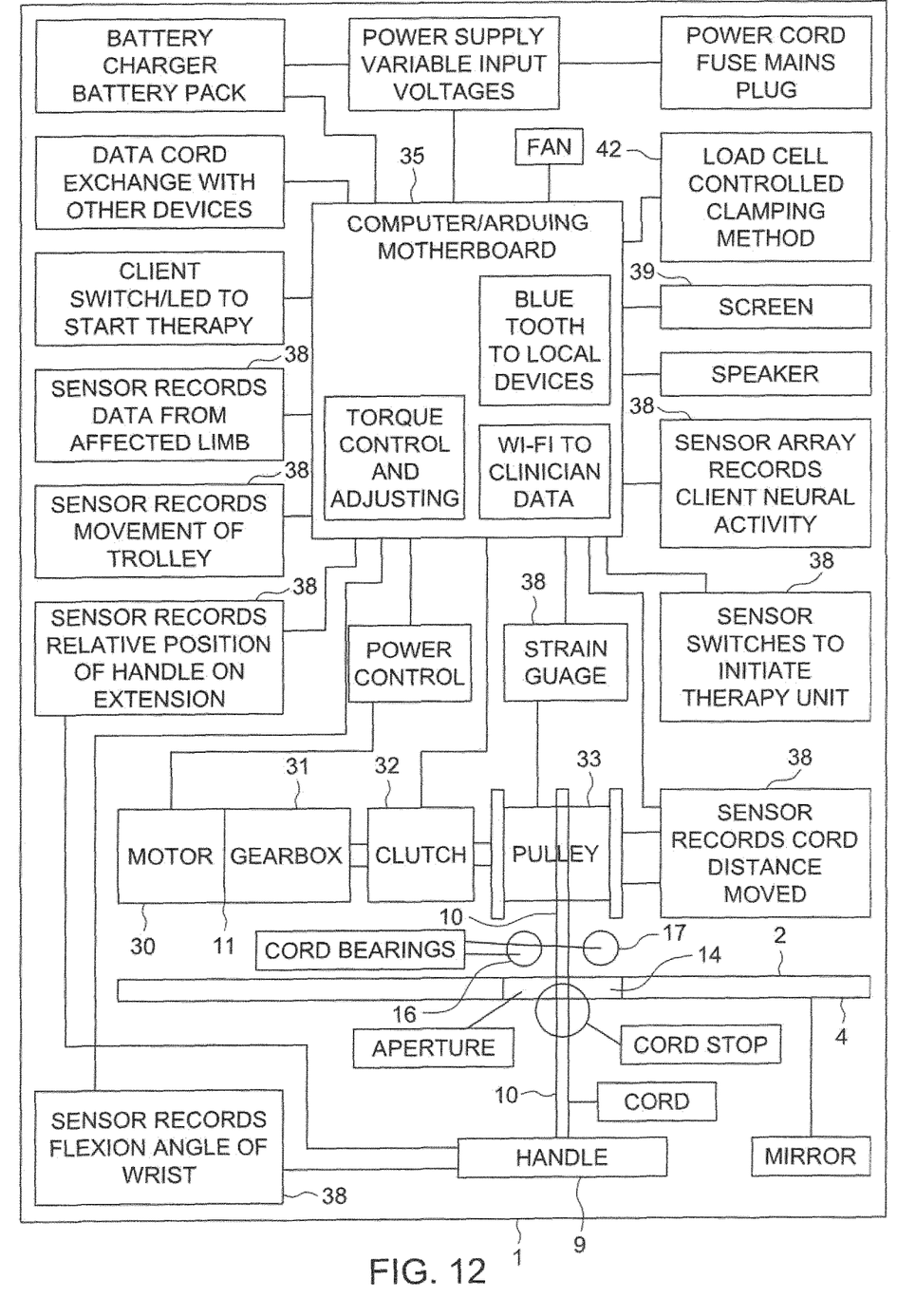
FIG. 12 is a schematic illustration of the mirror therapy device.

Referring in particular to FIG. 12, the resistance element 11 for the exercise apparatus 8 has a motor 30 and associated gearbox 31 connected by a clutch 32 with a pulley 33 on which the cord 10 is wound. A controller 35 incorporating a processor is connected to the motor 30 to control operation of the motor 30 and to the clutch 32 to control and adjust the torque applied to the pulley 33 to provide a resistance to pulling the cord 10 from the pulley 33 and to maintain this load during the return of the cord 10 onto the pulley 33 when returning the cord 10 from an extended position to a retracted wound-up position on the pulley 33. The resistance load can be remotely or locally adjusted by software or by an electronic control knob.

Various sensors 38 are connected to the controller 35, the sensors are associated with the exercise apparatus 8 to sense selected operating parameters of the exercise apparatus 8 and also to take selected physiological measurements of the patient using the device 1 associated with both the healthy limb and the affected limb. Any desired sensors may be provided, for example to record data from an injured limb of the patient, the relative position of the handle 9 on extension, the flexion angle of the wrist of the patient gripping the handle 9, recordal of neural activity of the patient, distance travelled by the load cord 10.

The sensed data can be displayed on a screen 39 which may conveniently be mounted on the divider panel 2. The controller 35 also has means to remotely communicate with a clinician who can review and evaluate the data collected and can also remotely set the operating parameters for the device 1 suitable for the patient using the device 1.

A slot 40 at a top of the divider panel 2 provides a handgrip for lifting and carrying the device 1.

In use, the mirror therapy device 1 can easily be set up in a patient's residence, being seated on and clamped to a table for example. The base unit 3 sits on the table and the table is clamped between the underside 6 of the base unit 3 and the clamp 5. The patient then places their injured limb on the base unit 3 and grabs the handle 9 of the exercise device 9 with their healthy limb. The patient then pulls the cord 10 by means of the handle 9 against the resistance load of the resistance element 11 to move the cord 10 between the retracted position shown in the drawings and an extended position. After extension of the cord 10 it is allowed return to the retracted position under continued load. Control of the resistance element 11 prevents a sudden snap back of the cord 10 and provides for a controlled wind up of the cord 10 on the pulley 33. The patient can view various operating parameters and physiological data on the display screen as they are using the device 1. This data can also be viewed remotely by a doctor, physiotherapist, or other clinician who is treating the patient and the device 1 may be adjusted if required remotely by the clinician to bring the patient through a course of treatment in their own residence or care environment.

It will be appreciated that the portable mirror therapy device of the invention allows a patient full access as required to the device 1 in their residence and under remote supervision from their doctor or clinician.

A second load cord may be provided on the reverse of the unit, that is above the base unit 3, which is engaged by the clients afflicted limb. A special feature of the load on this cord is that it may not be equal to the load on the non afflicted limb. The limb may be attached to the load cord via the clients natural grip or may be secured to clients limb by a binding fixture such as a Velcro (registered Trade Mark) strap for instance. In this way the client may exercise both left and right limbs simultaneously with different assigned loads for each limb.

It is an important feature that the speed of rewinding of the load cord 10 is set to govern the speed at which the patient returns the load handle 9 to the start position following each extension. This return half of the exercise is also under the prescribed load and is as important for physiological benefit as the preceding extension.

It is envisaged that the maximum extension of each load cord 10 would be set at approx. 1250 mm and the rewinding speed would be set at approx. 3.5 seconds. This slow rewind speed provides a safety feature in that if either of the load handles 9 were to slip from the patients grip then either one or both of the cords 10 will rewind slowly to the start position and are not able to snap back to the retracted start position violently.

The clamp 5 shown in the embodiment described is a simple manually operated G-clamp type with a disc and screw clamp. However this may not be suitable for all users, many of whom will have limited upper limb dexterity and strength.

In another embodiment of the invention it is proposed to provide a power driven clamp which is operable to clamp the device 1 to a support such as a table top or worktop and release the clamp after use. It is proposed to provide an internal motor gearbox driven screw that tightens two clamping elements located on the divider panel 2 and beneath the base unit 3. Electrical power is supplied by the user by means of a switch to clamp and declamp the device 1 on the support. A sensor connected to the controller 35 is used to regulate the clamping pressure to an appropriate level (as indicated at 42 in FIG. 12). This power assisted clamping is particularly appropriate for persons with an afflicted upper limb and reduced dexterity. Other attachment devices for securing the mirror therapy device 1 on a support are also possible, such as a suction clamp or magnetic clamp for example.

Figure 13:
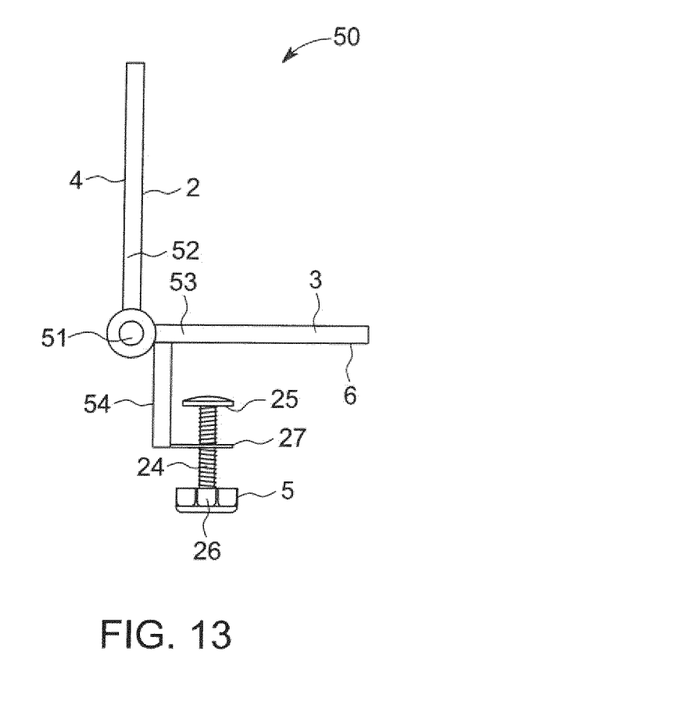
FIG. 13 is a schematic side elevational view of another mirror therapy device.
Figure 14:
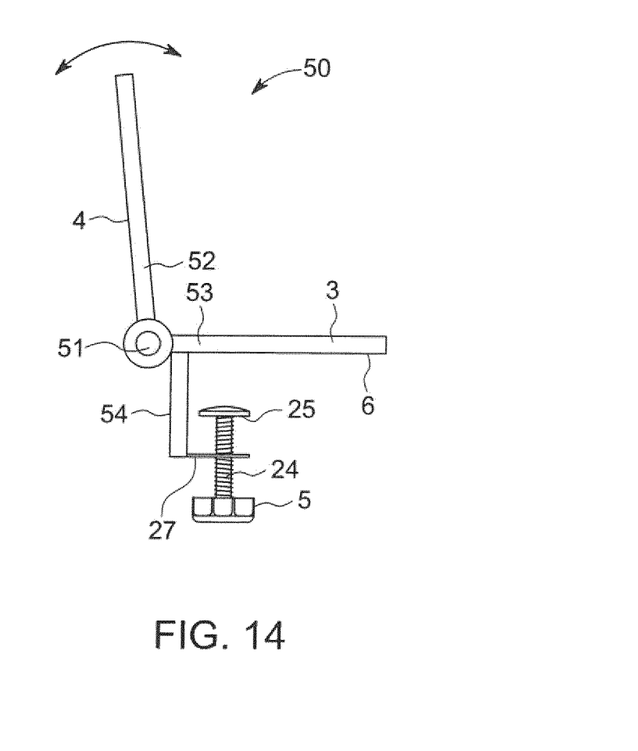
FIG. 14 is a view similar to FIG. 13, showing the mirror therapy device of FIG. 13 in another position of use.

Referring now to FIG. 13 and FIG. 14 there is shown another mirror therapy device according to the invention, indicated generally by the reference numeral 50. Parts similar to those described previously are assigned the same reference numerals. For simplicity the exercise apparatus 8 is not shown in these drawings. In this case the divider panel 2 is hingedly connected to the base unit 3 by means of a hinge 51 connecting a bottom 52 of the base unit 2 and an inner end 53 of the base unit 3. Thus the divider panel 2 is adjustable on the base unit 3, the hinge 51 allowing tilting of the divider panel 2 on the base unit 3 as shown in FIG. 14. A downwardly extending flange 54 on the underside 6 of the base unit 3 at the inner end 53 carries the clamps 5.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described which may be varied in both construction and detail within the scope of the appended claims.

The invention claimed is:

1. A portable mirror therapy device for use in a limb rehabilitation of a patient, the device comprising:
    a divider panel;
    a base unit to support the divider panel in an upright position to define two adjacent limb receiving spaces at opposite sides of the divider panel;
    a mirror on one face of the divider panel;
    an attachment device for rigidly securing the base unit to a support,
    an exercise apparatus which includes a limb engaging member at a mirror side of the divider panel,
    the exercise apparatus comprising a resistance load training system,
    the resistance load training system comprising a load cord extending from the limb engaging member to a resistance element, wherein the load cord is articulated through an aperture in the divider panel, the resistance element being mounted on an opposite side of the divider panel to the mirror.

2. The portable mirror therapy device as claimed in claim 1 wherein the attachment device is selectively engageable with the support.

3. The portable mirror therapy device as claimed in claim 1 wherein the load cord is movable between a retracted position and an extended position, the load cord being biased towards the retracted position, means being provided to control a rate at which the load cord returns from the extended position to the retracted position.

4. The portable mirror therapy device as claimed in claim 1 wherein the resistance element has a motor, a gearbox and clutch arrangement to control the rate at which the load cord returns from the extended portion to the retracted position.

5. The portable mirror therapy device as claimed in claim 1 wherein the attachment device is adjustable.

6. The portable mirror therapy device as claimed in claim 1 wherein the attachment device is movable between an engaged position with the support and a release position.

7. The portable mirror therapy device as claimed in claim 1 wherein the attachment device is a clamp.

8. The portable mirror therapy device as claimed in claim 1 wherein the mirror therapy device includes one or more sensors associated with the exercise apparatus and/or the patient to sense selected operating parameters of the exercise apparatus and/or take selected physiological measurements of the patient, the sensors being connected to an associated controller.

9. The portable mirror therapy device as claimed in claim 8 wherein the controller is operable to record data received from the sensors.

10. The portable mirror therapy device as claimed in claim 8 wherein the physiological measurements include patient neural activity.

11. The portable mirror therapy device as claimed in claim 8 wherein the sensor and controller are operable to record the distance travelled by the load cord.

12. The portable mirror therapy device as claimed in claim 8 wherein the sensor and the controller are operable to record the position of the limb engaging member.

13. The portable mirror therapy device as claimed in claim 8 wherein the sensor and the controller are operable to record a flexion angle of a wrist of a patient's hand holding the limb engaging member.

14. The portable mirror therapy device as claimed in claim 8 wherein the controller is connected to a display screen on the divider panel to display sensed data to the patient using the mirror therapy device.

15. The portable mirror therapy device as claimed in claim 8 wherein means is provided for remotely controlling the exercise apparatus.

16. The portable mirror therapy device as claimed in claim 1 wherein the divider panel is adjustable on the base unit.

17. The portable mirror therapy device as claimed in claim 16 wherein the divider panel is hingedly connected to the base unit for tilting the divider panel on the base unit.

18. The portable mirror therapy device as claimed in claim 1 comprising a motor linked to a gearbox and clutch contained in a housing mounted on the opposite side of the divider panel to the mirror, wherein the clutch is mechanically connected to the load cord which passes through the aperture in the divider panel and mirror, wherein the load cord is pulley guided, wherein the limb engaging member is a grip handle, wherein the grip handle is at a free end of the load cord and constructed from non-slip material, sensors which detect user limb data during exercise and transfer the data electronically to a processor of a controller contained in a housing which includes a transmitter and receiver to wirelessly send data to remote processors, wherein the attachment device comprises a set of adjustment screw handle clamps attached to the base unit or divider panel, a recessed handle in the divider panel and a carry case for reception and transport of the mirror therapy device.

19. A portable mirror therapy device for use in a limb rehabilitation of a patient, the device comprising:
   a divider panel;
   a base unit to support the divider panel in an upright position to define two adjacent limb receiving spaces at opposite sides of the divider panel;
   a mirror on one face of the divider panel;
   an attachment device for rigidly securing the base unit to a support,
   an exercise apparatus which includes a limb engaging member at a mirror side of the divider panel,
   the exercise apparatus comprising a resistance load training system, the resistance load training system comprising a load cord extending from the limb engaging member to a resistance element, wherein the load cord is articulated through an aperture in the divider panel, the resistance element being mounted on an opposite side of the divider panel to the mirror,
   the load cord being movable between a retracted position and an extended position, the load cord being biased towards the retracted position, means being provided to control a rate at which the load cord returns from the extended position to the retracted position, wherein the means comprises a motor, a gearbox and clutch arrangement to control the rate at which the load cord returns from the extended position to the retracted position.

* * * * *